United States Patent
Kamaguchi et al.

(10) Patent No.: US 7,255,921 B2
(45) Date of Patent: Aug. 14, 2007

(54) NON-GELATINOUS CAPSULE SHELL COMPOSITION AND A CAPSULE FORMED FROM THE SAME

(75) Inventors: Ryosei Kamaguchi, Osaka (JP); Takashi Shiomi, Osaka (JP); Yasuo Uehara, Osaka (JP)

(73) Assignee: Morishita Jintan Co., Ltd., Osaks-Shi (JP)

( * ) Notice: Subject to any disclaimer, the term of this patent is extended or adjusted under 35 U.S.C. 154(b) by 15 days.

(21) Appl. No.: 10/495,913

(22) PCT Filed: Nov. 22, 2002

(86) PCT No.: PCT/JP02/12220

§ 371 (c)(1),
(2), (4) Date: Sep. 30, 2004

(87) PCT Pub. No.: WO03/043609

PCT Pub. Date: May 30, 2003

(65) Prior Publication Data

US 2005/0069579 A1 Mar. 31, 2005

(30) Foreign Application Priority Data

Nov. 22, 2001 (JP) ............................. 2001-357050

(51) Int. Cl.
- *B32B 9/02* (2006.01)
- *C08L 3/02* (2006.01)
- *A61K 9/48* (2006.01)
- *A61K 9/50* (2006.01)

(52) U.S. Cl. .................. 428/402; 428/402.2; 424/451; 426/96; 106/203.1; 106/205.72; 106/215.5; 106/217.01; 106/217.2

(58) Field of Classification Search ............. 106/203.1, 106/205.72, 215.5, 217.01, 217.2; 424/451; 428/35.7, 402, 402.2; 426/96
See application file for complete search history.

(56) References Cited

U.S. PATENT DOCUMENTS

| | | | | |
|---|---|---|---|---|
| 3,971,852 A | * | 7/1976 | Brenner et al. | 426/103 |
| 6,340,473 B1 | * | 1/2002 | Tanner et al. | 424/451 |
| 6,348,264 B1 | * | 2/2002 | Abou-Nemeh et al. | 428/402 |
| 6,375,981 B1 | * | 4/2002 | Gilleland et al. | 424/452 |
| 2002/0029750 A1 | * | 3/2002 | Taylor | 119/843 |
| 2005/0196437 A1 | * | 9/2005 | Bednarz et al. | 424/451 |

FOREIGN PATENT DOCUMENTS

| | | |
|---|---|---|
| EP | 1 038 521 | 9/2000 |
| JP | 8-509018 | 9/1996 |
| JP | 2000-202003 | 7/2000 |
| JP | 2000-355534 | 12/2000 |
| WO | WO94/23593 | 10/1994 |

* cited by examiner

*Primary Examiner*—David M. Brunsman
(74) *Attorney, Agent, or Firm*—Hamre, Schumann, Mueller & Larson P.C.

(57) ABSTRACT

Non-gelatinous capsule film compositions containing as the base a starch hydrolyzate having an average DE of less than 10 and an average molecular weight of not more than 30,000. These non-gelatinous capsule film compositions have stable moisture absorbing/releasing properties and strength to such extent as sufficiently withstanding the production and storage as products and yet achieve excellent disintegration properties in vivo. Also, capsules produced by using the non-gelatinous capsule film compositions as described above are provided.

10 Claims, 2 Drawing Sheets

NON-GELATINOUS CAPSULE SHELL COMPOSITION AND A CAPSULE FORMED FROM THE SAME

TECHNICAL FIELD

The present invention relates to a non-gelatinous capsule shell composition used for foods, pharmaceuticals, quasi-drugs and the like, and a capsule formed from the same.

BACKGROUND ART

As a shell material of a capsule used for foods, pharmaceuticals, quasi-drugs and the like, a gelatin has been mainly used in view of rapid disintegrability in the body, high shell strength and stable moisture absorbing/releasing properties.

However, since gelatin is animal protein from livestock, such as cow, swine, poultry and the like, it is difficult to contain a substance that reacts with a protein as a capsule content therein. It is problem that the gelatin shell is easily insoluble or brittle with time and the heat resistance thereof is degraded when the moisture is increased. There have been cases that gelatin is incepted to have an allergy thereto and is restricted to use religiously or from vegetarism. In addition, recently, it has been difficult to use gelatin for the reason of infection or contamination of livestock diseases, such as mad cow disease (BSE), foot and mouth disease to human.

Therefore, it has been required to develop non-gelatinous capsule shell without using gelatin as a base.

Examples of the non-gelatinous capsule shells include a capsule shell containing water-insoluble agar as a base (for example, described in Japanese Patent Kokai Publication Nos. 193216/1989, 65222/1993, 196478/1995, 25228/1997, 253112/1999 and the like). However, when applying the capsule shell to foods, quasi-drugs and pharmaceuticals, it is difficult to rapidly release them in the body because of bad disintegrability thereof in the body.

A capsule shell containing carrageenan, polysaccharides and polyhydric alcohols as a base (described in Japanese Patent Kokai Publication No. 10508/1986) and a capsule shell obtained by gelling water-soluble base, such as hydroxypropylmethylcellulose, gellan gum or polyvinyl alcohol, by a gelling agent, such as carrageenan (described in Japanese Patent Kokai Publication Nos. 208458/1996, 291928/1998, 170137/2001 and the like), are disclosed. In these capsule shells, since high strength gel is formed by the base, the capsule strength is high, but the disintegration of the capsule shell is difficult, and the rapid disintegrability in the body is not sufficiently obtained. On the other hand, when using a base to low strength gel, the disintegration of the capsule shell is improved, but the capsule strength is low, and it is difficult to produce a capsule product. In addition, the capsule shell is broken after producing, and the capsule content leaks.

In U.S. Pat. No. 6,214,376, a capsule shell containing carrageenan and starch hydrolyzate, such as dextrin having a DE of not less than 10 is disclosed. However, the capsule is brittle and the moisture absorbing/releasing properties are increased, which causes the cracking or softening and stickiness of the capsule shell, and the storage stability is degraded.

As described above, in the conventional well-known technique, it has been difficult to provide a capsule shell that both the strength and easy disintegrability of the capsule shell, which are contrary to each other, can be accomplished and the quality can be retained by stabilizing the moisture absorbing/releasing properties.

DISCLOSURE OF INVENTION (Subject that the Invention is to Solve)

A main object of the present invention is to provide a non-gelatinous capsule shell composition having a strength durable to production and storage as the product of the capsule, stable moisture absorbing/releasing properties and excellent disintegrability in the body, and a capsule formed from the non-gelatinous capsule shell composition.

(Means of Solving the Subject)

In order to accomplish the object, the present inventors have studied the capsule shell composition. As a result, they have found that it is suitable for producing a capsule having easy disintegrability to use easily-water-soluble base at high content in a capsule shell composition. Moreover, they have studied vegetable materials that can retain sufficiently low viscosity to easily form a capsule by using at high content even if the solid content is high, and that have stable moisture absorbing/releasing properties. As a result, they have found to accomplish the object by using a starch hydrolyzate having low molecular weight as a base and optimizing the DE (dextrose equivalent) thereof.

The present invention provides a non-gelatinous capsule shell composition comprising a starch hydrolyzate as a base. Particularly, the present invention provides a non-gelatinous capsule shell composition comprising a starch hydrolyzate as a base and a gelling agent. In the present invention, the starch hydrolyzate having an average DE of less than 10 and an average molecular weight of not more than 30,000 is suitably used. The non-gelatinous capsule shell composition comprises the gelling agent and a gelation aid, and optionally a shell reinforcer and a plasticizer.

In addition, the present invention provides a capsule formed from the non-gelatinous capsule shell composition.

(Effect of the Invention)

According to the non-gelatinous capsule shell composition of the present invention using easily-water-soluble starch hydrolyzate, which is vegetable substance, as a base, the problem by using a gelatin can not be only solved, but a capsule having high strength, easy disintegrability in the body and excellent storage stability by stable moisture absorbing/releasing, which can not accomplished by the conventional non-gelatinous capsule, can be provided.

In present invention, the non-gelatinous capsule shell composition can comprise various additives, such as an enteric material, sweetening material and colorant, in order to impart the desired properties to the resulting capsule as the same as the conventional gelatinous capsule, and in the production of the capsule, the apparatus for the conventional gelatinous capsule can be used.

BEST MODE FOR CARRYING OUT THE INVENTION

The present invention will explain briefly as follows.

Non-gelatinous Capsule Shell Composition (1) Base

The capsule shell composition of the present invention comprises a starch hydrolyzate, which is easily water-soluble, as a base.

The starch hydrolyzate suitably used as the base is water-soluble, and has an average molecular weight of not more than 30,000, preferably 100 to 30,000.

In the capsule shell composition of the present invention, the starch hydrolyzate as a base is contained in an amount of not less than 50% by weight, preferably 55 to 65% by weight, based on total weight of the solid content in the capsule shell composition. In order to produce a capsule easily disintegrated, it is desired for the starch hydrolyzate to maintain low viscosity when used as an aqueous solution having high content.

Therefore, the starch hydrolyzate used preferably has a viscosity of 40% aqueous solution of not more than 300 mPa·s at 80° C.

Examples of the starch hydrolyzates suitably used as the base include, for example, soluble starch, dextrin and mixture thereof (such as "Stabilose", "Pinedex" (trade name); molecular weight Mw=100 to 40,000, which are commercially available from Matsutani Chemical Industry Co., Ltd.).

Figure 2:
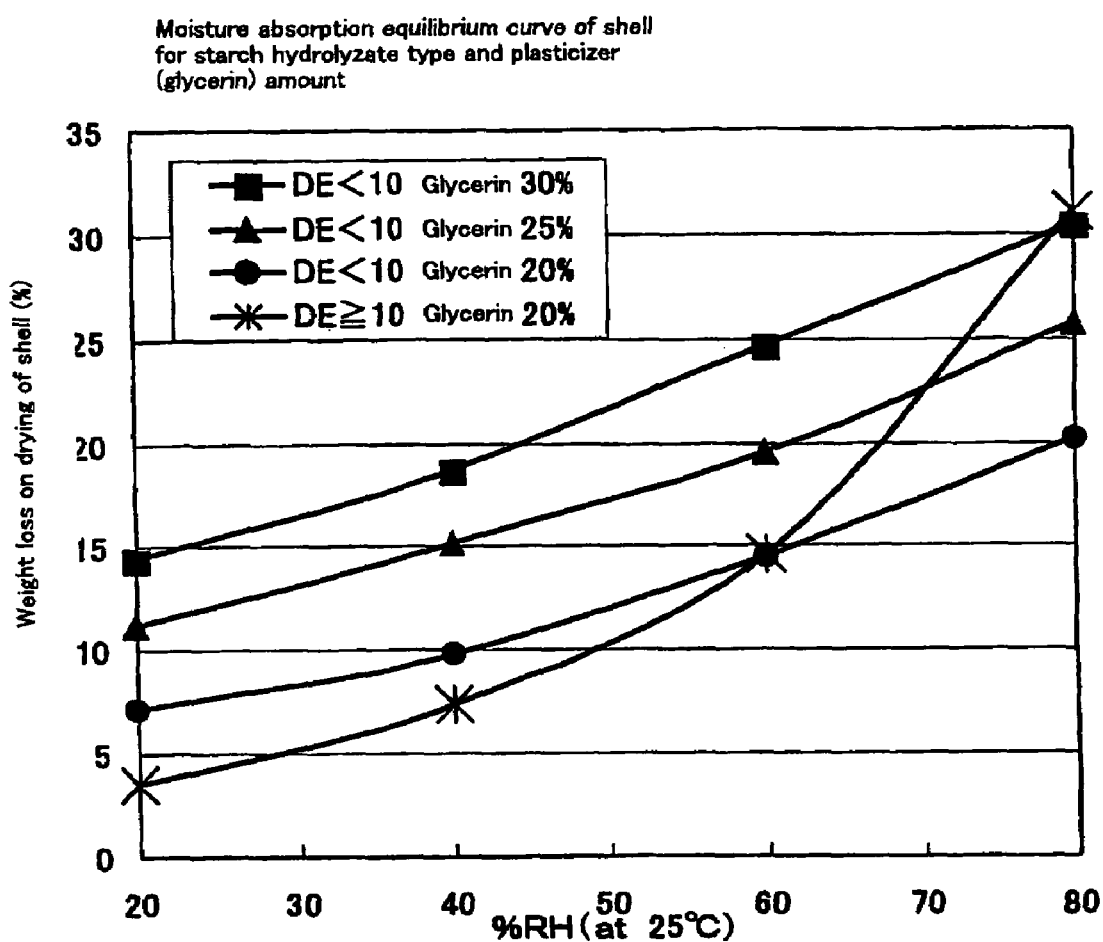
FIG. 2 is a graph illustrating the correlation of the humidity with the decrement of moisture (weight loss on drying) of the shell in the capsule of the present invention comprising as a base two starch hydrolyzates having different DE.

In the present invention, it was attempted to optimize a dextrose equivalent DE of starch hydrolyzate used as the base in order to provide a capsule having storage stability by stable moisture absorption and release. Capsule shell compositions were prepared by using two starch hydrolyzates having different DE (one has DE of less than 10, and the other has DE of not less than 10) and the moisture content of the capsule shell at different humidity conditions was determined by measuring a decrement of moisture (weight loss on drying) of the shell in absolute drying condition at 120° C. for 24 hours. As the result, when using the starch hydrolyzate having DE of not less than 10, the weight loss was not less than 25% at a humidity of 20 to 80% RH. On the other hand, when using the starch hydrolyzate having DE of less than 10, the weight loss was not more than 15% (as shown in FIG. 2). That is, when using the starch hydrolyzate having DE of less than 10 as a base, the moisture absorption and release of the capsule shell composition is stabilized. As the result, it was possible to prevent the capsule shell from cracking by brittleness at low humidity and from degrading the product quality by softening and stickiness at high humidity.

Therefore, in the present invention, it is desired for the starch hydrolyzate used for the base to have a DE of less than 10. The starch hydrolyzate having the DE of less than 10 may be used alone or optionally in combination with the starch hydrolyzate having DE of not less than 10, that is, high hydrolyzability. If using the combination, it is desired to select the starch hydrolyzate having high hydrolyzability and the starch hydrolyzate having low hydrolyzability such that the mixture of the starch hydrolyzates has an average DE of less than 10, the average molecular weight of not more than 30,000 and the viscosity of 40% aqueous solution of not more than 300 mPa·s at 80° C. Examples of the starch hydrolyzates having high hydrolyzability include, for example, maltodextrin, which is commercially available from Matsutani Chemical Industry Co., Ltd. under the trade name "TK-16", and the like. The amount of the maltodextrin as the starch hydrolyzates having high hydrolyzability is preferably not more than 35% by weight, more preferably not more than 25% by weight, based on the total weight of the solid content in the capsule shell composition.

The capsule shell composition of the present invention may optionally comprise a shell reinforcer in order to improve the disintegrability of the capsule itself in the body and the capsule shell strength, in addition to the gelling agent and gelation aid used together with the base.

(2) Gelling Agent and Gelation Aid

As the gelling agent, polysaccharides derived from plant, which melts at a temperature not more than 80° C., are suitably used, and examples thereof include one or combination of two or more selected from the group consisting of furcellan, carrageenan, pectin, curdlan, psyllium seed gum, xanthan gum, locust bean gum, guar gum and gelled starch. In the gelling agent, a weight ratio of one or combination of two or more selected from the group consisting of furcellan, LM pectin, curdlan, psyllium seed gum, mixture of xanthan gum and locust bean gum, mixture of xanthan gum and guar gum, mixture of xanthan gum and guar gum hydrolyzate, and gelled starch to the carrageenan may be within the range of 6:4 to 9:1. As the gelling agent, one or mixture of two or more gelled starches selected from the group consisting of acid hydrolyzed starch and white dextrin may be used.

The gelling agent is contained in an amount of 0.5 to 30% by weight, preferably 1 to 15% by weight, based on total weight of the solid content in the capsule shell composition.

In the capsule shell composition of the present invention, it is desired to use the gelation aid consisting of monovalent ion or divalent ion, preferably one or combination of two or more selected from the group consisting of a potassium ion, a sodium ion, a calcium ion and an ammonium ion, together with the gelling agent in order to improve the formability of the capsule shell. The gelation aid is contained in an amount of 0.1 to 10% by weight, preferably 0.5 to 5% by weight, based on total weight of the solid content in the capsule shell composition.

(3) Shell Reinforcer

Examples of the suitable shell reinforcer include monosaccharides, such as dextrose, fructose, glucose, galactose; oligosaccharide, and disaccharides, such as sucrose, maltose, trehalose, coupling suger; polysaccharides, such as pullulan, gum arabic, arabinogaractan, cellulose and derivatives thereof; and sugar alcohol, such as sorbitol, maltitol (reduced maltose syrup), lactitol, palatinit, xylitol, mannitol, galactitol. The shell reinforcer may be used alone or in combination with two or more thereof. The shell reinforcer is contained in an amount of 0.1 to 50% by weight, preferably 0.5 to 30% by weight, based on total weight of the solid content in the capsule shell composition.

(4) Plasticizer

In the present invention, the capsule shell composition may optionally contain the plasticizer in addition to the above components. Examples of the plasticizers suitably used include one or combination of two or more selected from the group consisting of polyhydric alcohols, such as glycerin, polyethylene glycol, propylene glycol, polypropylene glycol. The plasticizer is contained in an amount of 10 to 40% by weight, preferably 15 to 30% by weight, based on total weight of the solid content in the capsule shell composition.

(5) Enteric Material and Additives

In the present invention, the capsule shell composition may optionally contain the enteric material as the same as the conventional capsule shell composition in order to form the enteric capsule. Examples of the enteric materials include pectin, alginic acid salt, methacrylic acid copolymer, hydroxypropylmethylcellulose phthalate, hydroxypropylmethylcelluloseacetate succinate, carboxyl methylethylcellulose, celluloseacetate phthalate and the like. The enteric material may be used alone or in combination with two or more thereof. The enteric material is contained in an amount of 0.5 to 20% by weight, preferably 1 to 20% by weight, based on total weight of the solid content in the capsule shell composition.

The capsule shell composition of the present invention may contain various additives, such as aromatic, sweetening material, colorant, antiseptic including paraben, which have been conventionally used in the art, in addition to the above components. The additives are contained in total amount of 0.01 to 10% by weight, preferably 0.1 to 5% by weight, based on total weight of the solid content in the capsule shell composition.

Capsule

By using the non-gelatinous capsule shell composition of the present invention, capsules having easy disintegrability in any form of hard capsule, soft capsule or micro-capsule can be provided. As non-limited examples of methods of producing the capsule include a method of producing a capsule having a particle diameter of 50μ to 10 mm described in Japanese Patent Kokai Publication No. 49154/1981, of which the content used is oily substance, such as purified vegetable oil, aromatic, oily vitamin, oil-soluble medicinal substance, unsaturated fatty acid or a derivative thereof;

a method of producing a capsule, of which the content contains a hydrophilic substance, described in Japanese Patent Kokai Publication Nos. 52639/1991 and 31352/1993; and a method of producing a capsule, of which the content contains bifidus (Lactobacillus bijidus), described in Japanese Patent Kokai Publication Nos. 151127/1986 and 69867/1995.

The capsule of the present invention may be a seamless capsule. The seamless capsule can be produce by a method of continuously producing seamless capsule by a dripping process using a multiple nozzle, for example, described in Japanese Patent Kokai Publication Nos. 22062/1983, 131355/1984, 52639/1991, 31352/1993, 69867/1995 and the like, but is not limited thereto. In the dripping process using a multiple nozzle, after a concentric multiple nozzle, which is doublet or more, is inserted into liquid oil flowing down at a constant rate, the content substance is ejected through an innermost nozzle and the non-gelatinous capsule shell composition is ejected through an outermost nozzle, simultaneously, at a constant rate to continuously produce spherical seamless capsule by interfacial tension applied between the liquid oil and shell substance.

The capsule of the present invention has a particle diameter after drying of 0.1 to 10 mm, preferably 0.3 to 8 mm. The capsule of the present invention has a shell thickness of 30 to 300 μm.

The capsule after producing may be used without drying the moisture in the capsule shell, or after drying the moisture by a conventional drying process or vacuum drying process, depending to purpose thereof.

The capsule of the present invention can be added to, for example, tablet or chewing gum, gumi, chocolate, hard candy and the like in a suitable amount.

EXAMPLES

The following Examples further illustrate the present invention in detail but are not to be construed to limit the scope thereto.

Example 1

The formulation for the capsule shell shown in Table 1 was mixed to prepare a non-gelatinous capsule shell composition. The MCT (Medium chain triglyceride) shown in Table 1 was prepared as a content in the capsule.

Figure 1:
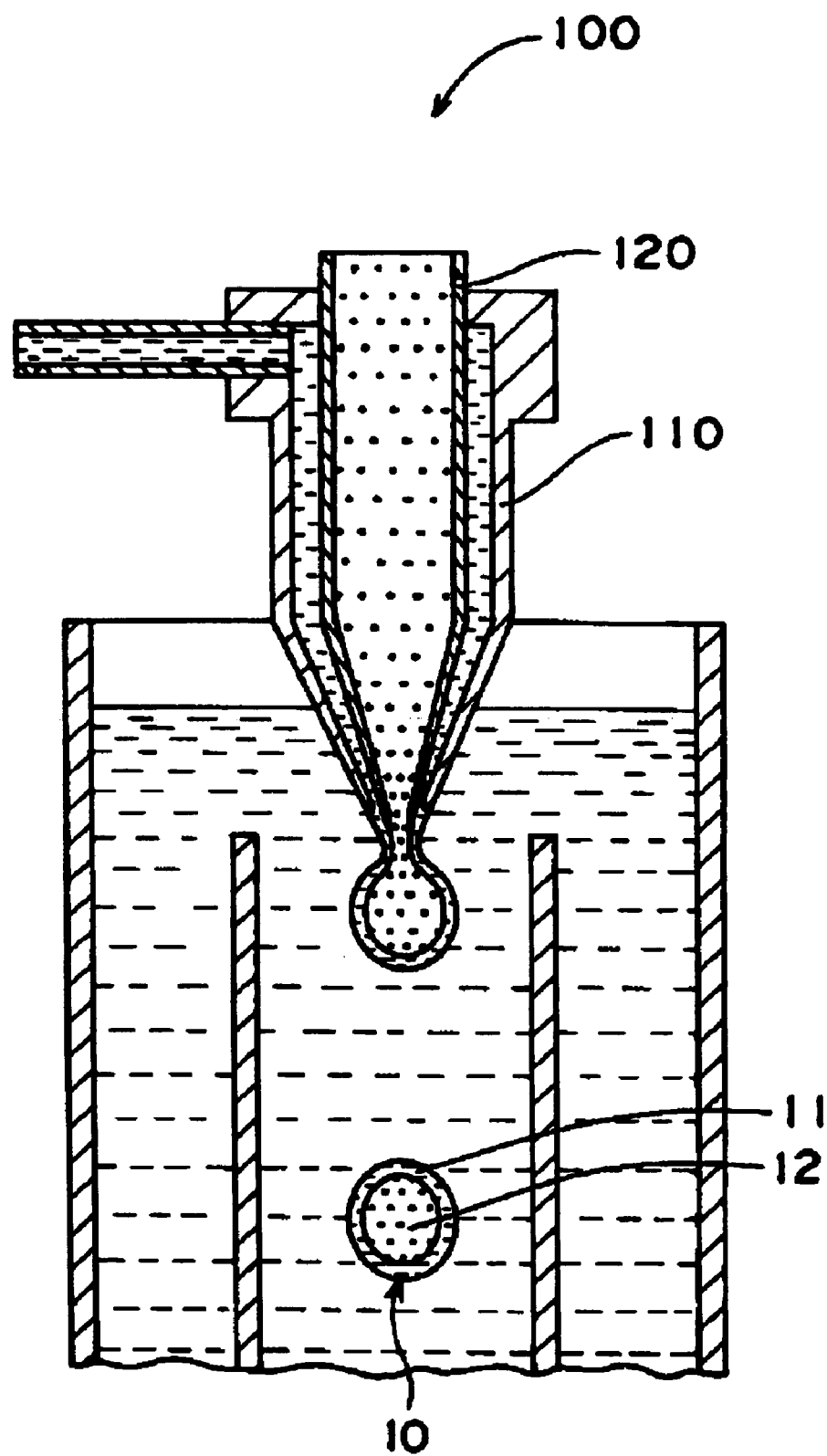
FIG. 1 is a schematic cross section illustrating one embodiment of the apparatus for making the capsule of the present invention (the apparatus for making the seamless capsule with doublet nozzle used for dripping process in Examples).

The shell composition and the content were applied to the machine 100 for producing the seamless capsule shown in FIG. 1 according to the following procedure to produce the capsule 10 of the present invention having doublet structure, in which the content 12 was contained in the capsule shell 11. The non-gelatinous capsule shell composition of the present invention heated to 70° C. was ejected through an outer nozzle of a concentric doublet nozzle and the content was ejected through an inner nozzle, simultaneously, to form a two-phase composite jet stream, followed by releasing the jet stream into a cooling solution (a vegetable oil cooled to the temperature of not more than 20° C.) to obtain the seamless capsule of the present invention. After drying the resulting capsule at the temperature and humidity condition of 25° C. and 50% RH by using a forced-air circulation oven, the capsule was used for the evaluation tests described later.

In the apparatus 100, the nozzle 110 for the content had an inner diameter $\Phi_1$ of 2 mm, the nozzle 120 for the shell had an inner diameter $\Phi_2$ of 4 mm. The resulting capsule 10 had a particle diameter $\Phi$ of 2 mm and a capsule shell thickness of 85 μm.

TABLE 1

| Composition | Amount |
|---|---|
| (Shell) | |
| Base: | |
| Maltodextrin ("Pinedex #2")* | 15.2% by weight |
| Gelling agent: | |
| κ-Carrageenan | 2.3% by weight |
| Locust bean gum | 0.1% by weight |
| Shell reinforcer: | |
| Glycerin | 4.5% by weight |
| Gelation aid: | |
| Potassium chloride | 0.4% by weight |
| Purified water | 77.5% by weight |
| Solid content | 22.5% |
| (Content) | |
| MCT (Medium chain triglyceride) | 100% by weight |

*commercially available from Matsutani Chemical Industry Co., Ltd.; average molecular weight = 1700; DE = 10 to 12

Example 2

The seamless capsule of the present invention was produced in the same way as described in Example 1, except that the formulations for the capsule shell and content shown in Table 2 were used. The resulting capsule 10 had a particle diameter Φ of 2 mm and a capsule shell thickness of 85 μm.

TABLE 2

| Composition | Amount |
| --- | --- |
| (Shell) | |
| Base: | |
| Soluble starch (Stabilose TA-13)** | 15.2% by weight |
| Gelling agent: | |
| κ-Carrageenan | 2.3% by weight |
| Locust bean gum | 0.1% by weight |
| Shell reinforcer: | |
| Glycerin | 4.5% by weight |
| Gelation aid: | |
| Potassium chloride | 0.4% by weight |
| Purified water | 77.5% by weight |
| Solid content | 22.5% |
| (Content) | |
| MCT (Medium chain triglyceride) | 100% by weight |

**commercially available from Matsutani Chemical Industry Co., Ltd.; average molecular weight = 20,000 to 30,000; DE = about 1

Example 3

The seamless capsule of the present invention was produced in the same way as described in Example 1, except that the formulations for the capsule shell and content shown in Table 3 were used. The resulting capsule 10 had a particle diameter Φ of 2 mm and a capsule shell thickness of 85 μm

TABLE 3

| Composition | Amount |
| --- | --- |
| (Shell) | |
| Base: | |
| Soluble starch (Stabilose TA-13)** | 14.1% by weight |
| Gelling agent: | |
| Furcellan | 2.3% by weight |
| Locust bean gum | 0.1% by weight |
| Shell reinforcer: | |
| Glycerin | 5.6% by weight |
| Gelation aid: | |
| Potassium chloride | 0.4% by weight |
| Purified water | 77.5% by weight |
| Solid content | 22.5% |
| (Content) | |
| MCT (Medium chain triglyceride) | 100% by weight |

Example 4

The seamless capsule of the present invention was produced in the same way as described in Example 1, except that the formulations for the capsule shell and content shown in Table 4 were used. The resulting capsule 10 had a particle diameter Φ of 2 mm and a capsule shell thickness of 85 μm.

TABLE 4

| Composition | Amount |
| --- | --- |
| (Shell) | |
| Base: | |
| Soluble starch (Stabilose TA-13)** | 14.1% by weight |
| Gelling agent: | |
| Furcellan | 1.3% by weight |
| κ-Carrageenan | 1.0% by weight |
| Locust bean gum | 0.1% by weight |
| Shell reinforcer: | |
| Glycerin | 5.6% by weight |
| Gelation aid: | |
| Potassium chloride | 0.4% by weight |
| Purified water | 77.5% by weight |
| Solid content | 22.5% |
| (Content) | |
| MCT (Medium chain triglyceride) | 100% by weight |

Example 5

The seamless capsule of the present invention was produced in the same way as described in Example 1, except that the formulations for the capsule shell and content shown in Table 5 were used. The resulting capsule 10 had a particle diameter Φ of 2 mm and a capsule shell thickness of 85 μm.

TABLE 5

| Composition | Amount |
| --- | --- |
| (Shell) | |
| Base: | |
| Soluble starch (Stabilose TA-13)** | 13.6% by weight |
| Gelling agent: | |
| Furcellan | 2.3% by weight |
| Locust bean gum | 0.1% by weight |
| Shell reinforcer: | |
| Glycerin | 5.6% by weight |
| Enteric material: | |
| Sodium alginate | 0.3% by weight |
| Gelation aid: | |
| Potassium chloride | 0.4% by weight |
| Calcium chloride | 0.2% by weight |
| Purified water | 77.5% by weight |
| Solid content | 22.5% |
| (Content) | |
| MCT (Medium chain triglyceride) | 100% by weight |

Example 6

The seamless capsule of the present invention was produced in the same way as described in Example 1, except that the formulations for the capsule shell and content shown in Table 6 were used. The resulting capsule 10 had a particle diameter Φ of 2 mm and a capsule shell thickness of 85 μm.

TABLE 6

| Composition | Amount |
|---|---|
| (Shell) | |
| Base: | |
| Soluble starch (Stabilose TA-13) | 12.0% by weight |
| Gelling agent: | |
| κ-Carrageenan | 1.0% by weight |
| Gelled soluble starch(NSP-70)*** | 4.5% by weight |
| Locust bean gum | 0.1% by weight |
| Shell reinforcer: | |
| Glycerin | 4.5% by weight |
| Gelation aid: | |
| Potassium chloride | 0.4% by weight |
| Purified water | 77.5% by weight |
| Solid content | 22.5% |
| (Content) | |
| 1-menthol | 20% by weight |
| MCT (Medium chain triglyceride) | 80% by weight |

***commercially available from Nippon Starch Chemical Co., Ltd.

Comparative Example 1

The seamless capsule for the control was produced in the same way as described in Example 1, except that the formulations for the capsule shell and content shown in Table 7 were used. The resulting capsule 10 had a particle diameter Φ of 2 mm and a capsule shell thickness of 85 μm.

TABLE 7

| Composition | Amount |
|---|---|
| (Shell) | |
| Base: | |
| Agar | 2% by weight |
| Plasticizer: | |
| Glycerin | 15% by weight |
| Purified water | 80% by weight |
| Solid content | 20% |
| (Content) | |
| MCT (Medium chain triglyceride) | 100% by weight |

Comparative Example 2

The seamless capsule for the control was produced in the same way as described in Example 1, except that the formulations for the capsule shell and content shown in Table 8 were used. The resulting capsule 10 had a particle diameter Φ of 2 mm and a capsule shell thickness of 85 μm.

TABLE 8

| Composition | Amount |
|---|---|
| (Shell) | |
| Base: | |
| Gelatin | 17% by weight |
| Plasticizer: | |
| Glycerin | 3% by weight |
| Purified water | 80% by weight |
| Solid content | 20% |

TABLE 8-continued

| Composition | Amount |
|---|---|
| (Content) | |
| MCT (Medium chain triglyceride) | 100% by weight |

Comparative Example 3

The seamless capsule for the control was produced in the same way as described in Example 1, except that the formulations for the capsule shell and content shown in Table 9 were used. The resulting capsule 10 had a particle diameter Φ of 2 mm and a capsule shell thickness of 85 μm

TABLE 9

| Composition | Amount |
|---|---|
| (Shell) | |
| Base: | |
| Gelatin | 17% by weight |
| Plasticizer: | |
| Glycerin | 3% by weight |
| Purified water | 80% by weight |
| Solid content | 20% |
| (Content) | |
| 1-menthol | 20% by weight |
| MCT (Medium chain triglyceride) | 80% by weight |

Evaluation Tests

With respect to the resulting seamless capsules of Examples 1 to 5 and Comparative Examples 1 to 2, the following tests (1) and (2) were conducted, and the results are shown in Table 10.

(1) Hardness

The hardness of the capsule was measured by using Rheo Meter CR-200D manufactured by Sun Scientific Co., Ltd. at compression mode. The pressure measuring stem "No. 1" having a diameter of 10 mm was used. The measurement was conducted by using 20 capsules for every sample, and the average is shown as the result of the capsule.

(2) Disintegration Test

The disintegrability of the capsule for the first solution and second solution was measured by the procedure of disintegration test and apparatus according to Japanese Pharmacopoeia (12th). The measurement was conducted by using 3 capsules for every sample, and the average is shown as the result of the capsule.

TABLE 10

| Sample No. | Capsule hardness (g) | Japanese Pharmacopoeia disintegration test results | |
|---|---|---|---|
| | | First solution | Second solution |
| Comparative Example 1 | 900 | Insoluble (No good) | Insoluble (No good) |
| Comparative Example 2 | 2100 | Dissolved (Good) | — |
| Example 1 | 970 | Dissolved (Good) | — |
| Example 2 | 1120 | Dissolved (Good) | — |
| Example 3 | 1170 | Dissolved (Good) | — |
| Example 4 | 1150 | Dissolved (Good) | — |
| Example 5 | 1220 | Insoluble (No good) | Dissolved (Good) |

As is apparent from Table 10, the seamless capsule of the present invention of Examples 1 to 4 have equal or higher capsule hardness and excellent disintegrability, as compared with the seamless capsule of Comparative Example 1 having the non-gelatinous shell of conventional composition. The seamless capsule of the present invention of Example 4 has the capsule hardness and disintegrability near to those of the seamless capsule of Comparative Example 2 having the non-gelatinous shell of conventional composition.

The seamless capsule of the present invention of Example 5 having the enteric shell was not dissolved in the first solution, but was rapidly dissolved in the second solution.

(3) Gas Permeability

In the capsules of Example 6 and Comparative Example 3, the gas permeability was evaluated by 7 panelists according to a organoleptic examination for comparing the degree of volatilization of 1-menthol, which is a content permeated through the capsule shell. The results are shown in Table 11.

TABLE 11

| Gas permeability test | | Panelist | | | | | | |
|---|---|---|---|---|---|---|---|---|
| results | | A | B | C | D | E | F | G |
| Answer | Com. Ex. 3 > Ex. 6 *1 | | o | | | | | |
| | Com. Ex. 3 < Ex. 6 *2 | | | o | o | | | |
| | Com. Ex. 3 = Ex. 6 *3 | o | | | o | | o | o |

*1: The capsule of Comparative Example 3 retains 1-menthol more strongly than that of Example 6.
*2: The capsule of Example 6 retains 1-menthol more strongly than that of Comparative Example 3.
*3: There is no difference between Comparative Example 3 and Example 6.

As is apparent from Table 11, the seamless capsule of the present invention of Example 6 has equal or lower gas permeability than the conventional seamless capsule having gelatin shell of Comparative Example 3. That is, the seamless capsule of the present invention has equal or higher retention of the content than the seamless capsule having gelatin shell of conventional composition.

The invention claimed is:

1. A non-gelatinous seamless capsule comprising a content and a capsule shell encapsulating the content, wherein the capsule shell comprises (a) a soluble starch or dextrin having an average dextrose equivalent DE of less than 10 and an average molecular weight of not more than 30,000 and (b) a gelling agent being a polysaccharide which melts at a temperature of not more than 80° C., and the seamless capsule is obtained by a dripping process using a multiple nozzle.

2. The non-gelatinous seamless capsule according to claim 1, wherein the soluble starch or dextrin (a) is contained in an amount of not less than 50%, based on total weight of a composition for the capsule shell.

3. The non-gelatinous seamless capsule according to claim 1, wherein the gelling agent is a polysaccharide, which is one or combination of two or more selected from the group consisting of furcellan, carrageenan, LM pectin, curdlan, psyllium seed gum, mixture of xanthan gum and locust bean gum, mixture of xanthan gum and guar gum, mixture of xanthan gum and guar gum hydrolyzate, and gelled starch.

4. The non-gelatinous seamless capsule according to claim 1, wherein the gelling agent is carrageenan, and a weight ratio of one or combination of two or more selected from the group consisting of furcellan, LM pectin, curdlan, psyllium seed gum, mixture of xanthan gum and locust bean gum, mixture of xanthan gum and guar gun, mixture of santhan gum and guar gum hydrolyzate, and gelled starch to the carrageenan is 6:4 to 9:1.

5. The non-gelatinous seamless capsule according to claim 1, wherein the gelling agent is one or combination of two or more selected from the group consisting of acid hydrolyzed starch and white dextrin.

6. The non-gelatinous seamless capsule according to claim 1, wherein the gelling agent comprises a gelation aid.

7. The non-gelatinous seamless capsule according to claim 6, wherein the gelation aid is one or combination of two or more selected from the group consisting of a potassium ion, a sodium ion, a calcium ion and an aminonium ion.

8. The non-gelatinous seamless capsule according to claim 1, wherein the gelling agent comprises a shell reinforcer.

9. The non-gelatinous seamless capsule according to claim 8, wherein the shell reinforcer is one or combination of two or more selected from the group consisting of monosaccharides, disaccharides, oligosaccharide, polysaccharides and sugar alcohol.

10. The non-gelatinous seamless capsule according to claim 8, wherein the shell reinforcer is a non-gelled polysaccharide, which is one or combination of two or more selected from the group consisting of pullulan, trehalose, gum arabic, arabinogaractan, cellulose and derivatives thereof.

* * * * *